United States Patent [19]

Duffy

[11] 4,283,324
[45] Aug. 11, 1981

[54] NAIL ENAMEL COMPOSITION

[75] Inventor: John A. Duffy, West Milford, N.J.

[73] Assignee: Avon Products, Inc., Suffern, N.Y.

[21] Appl. No.: 100,241

[22] Filed: Dec. 4, 1979

[51] Int. Cl.$^3$ .................. C08F 61/00; C09D 3/48; C08F 216/00

[52] U.S. Cl. .................. 260/31.2 N; 260/33.6 UA; 424/61; 428/15; 525/58; 525/157; 525/189; 525/472; 525/512

[58] Field of Search .................. 428/15; 525/58, 157, 525/189, 472, 510–512; 424/61; 260/31.2 N, 33.6 UA, 15

[56] References Cited

U.S. PATENT DOCUMENTS

| | | | |
|---|---|---|---|
| 1,907,554 | 5/1933 | Moss et al. | 260/15 |
| 2,423,565 | 7/1947 | Rodman | 525/58 |
| 3,959,193 | 5/1976 | Putman et al. | 260/15 |
| 4,126,144 | 11/1978 | Duarte | 424/61 |
| 4,179,304 | 12/1979 | Rossomando | 260/17 R |

FOREIGN PATENT DOCUMENTS

109560  1/1940  Australia .................. 424/61

OTHER PUBLICATIONS

Derwent Abs. 75586B/42, Oct. 11, 1979 Polychrome Corp.
Derwent Abs. 1193C/01, Apr. 16, 1979 Foundry Prod. Des.

*Primary Examiner*—Joseph L. Schofer
*Assistant Examiner*—Herbert J. Lilling
*Attorney, Agent, or Firm*—Sigalos & Levine

[57] ABSTRACT

A nitrocellulose-free nail enamel composition comprising a polyvinyl butyral resin as the film-forming agent, a compatible modifier resin, and a compatible cosmetic solvent.

5 Claims, No Drawings

NAIL ENAMEL COMPOSITION

BACKGROUND OF THE INVENTION

Nail enamel compositions (i.e., film-forming nail coatings) such as base coats, top coats, clear nail enamels, pigmented, clear and frost nail enamels, nail menders, and the like utilize nitrocellulose (cellulose nitrate) as the conventional and major film-forming portion thereof.

While generally suitable, nail enamels utilizing nitrocellulose as the film-forming agent tend to yellow since, with time, the nitrocellulose will degrade and turn yellow. This is, of course, undesirable since it causes the nail enamel products to undergo color changes. Efforts to overcome this yellowing problem have not been successful and presently the problem is mainly treated by trying to minimize the time nail enamel products have to remain "on the shelf" before use.

In addition to its yellowing properties, the use of nitrocellulose, because of its high glass transition point, requires the addition of plasticizers to nail enamel compositions. Such plasticizers as camphor, dibutyl phthalate, and the like must be added in significant amounts to the compositions and this acts to complicate formulation in terms of trying to obtain the gloss, wear, viscosity, and other properties desired in nail enamel compositions.

Finally, nitrocellulose is highly flammable and care must be taken by the user when applying nitrocellulose-based nail enamels to ensure that it is not used near an open flame.

SUMMARY OF THE INVENTION

The present invention provides nail enamel products which are non-yellowing, use a non-flammable film-former, and of simpler formulation while at the same time having gloss, wear, and other characteristics equal to or better than the present nitrocellulose based products.

Briefly, the present invention comprises a nitrocellulose-free nail enamel product comprising a polyvinyl butyral resin as the film-forming resin, a compatible modifier resin, and a compatible cosmetic solvent.

DETAILED DESCRIPTION

While the instant invention is applicable to all types of nail enamel compositions as discussed above, it will be further described in connection with base coats. These are normally products which do not contain any pigment and, hence, yellowing is a more severe problem since it is not masked to any extent by coloring.

The essential and key component of the base coat, and other nail enamel compositions of this invention, is a polyvinyl butyral resin which is used as the film-forming agent in the product and the absence of nitrocellulose and its plasticizers. Any commercially available polyvinyl butyral resin can be utilized, including those used as glass laminating resins. As to proportions of polyvinyl butyral in the base coat, it can be added in the amounts conventionally added in nitrocellulose formulations, i.e., from about 5 to 20%, preferably 8 to 12%, by weight based on 100% by weight of the total composition. As in conventional nitrocellulose formulations, the amount of polyvinyl butyral resin can be varied to achieve a wide range of viscosity and, subsequently, application properties.

In the base coat the other necessary components are those conventionally required in existing compositions. Namely, a compatible modifier resin and solvent.

As to the modifier resin it can be any commonly used to improve adhesive, hardness, gloss and/or wear resistance and the like but aryl-sulfonamide-formaldehyde resins, such as p-toluene-sulfonamide-formaldehyde, are preferred because they best promote high gloss and good adhesion. The amount of such resin in the product can be widely varied to give the viscosity, gloss, and the like characteristics desired, but generally such modifier resins are used in an amount no greater than about one part by weight for each part by weight of the polyvinyl butyral.

With respect to the solvent, it is again conventional in that the usual ester solvents commonly employed in nail enamels are used. These can include most suitably, ethyl and n-butyl acetate although other solvents such as toluene can also be used. It is preferred to use a combination of ethyl and n-butyl acetate. The solvent comprises the major constituent of the base coat composition; some about 60% by weight or more thereof.

Other minor and conventional constituents can be added to the base coat in their usual amounts and for their usual effect.

With other nail enamel compositions such as pigmented nail enamels, nail menders, and the like, the proportions of polyvinyl butyral modifier resin, and solvent are varied to give the properties desired. What is important is that no nitrocellulose or the plasticizer required therefor are included in the formulations.

It will also be understood that the other components required in such products are also included for their usual effect and in their usual proportions. Thus, for example, in a typical pigmented nail enamel there will conventionally also be included a coloring agent, a thixotropic agent (such as bentonite) for suspension of the coloring agent, and an alcohol such as ethanol or isopropanol.

While the invention has been described in connection with a preferred embodiment, it is not intended to limit the scope of the invention to the particular form set forth, but, on the contrary it is intended to cover such alternatives, modifications, and equivalents as may be included within the spirit and scope of the invention as defined by the appended claims.

What is claimed is:

1. A nitrocellulose-free nail enamel composition comprising a polyvinyl butyral resin, an aryl-sulfonamide-formaldehyde resin, and a compatible solvent; said solvent being the major constituent of the composition.

2. The composition of claim 1 wherein the modifier resin is an aryl-sulfonamide-formaldehyde and the solvent is an ester solvent.

3. The composition of claim 1 wherein the solvent comprises a combination of ethyl acetate and n-butyl acetate.

4. A nitrocellulose-free nail enamel composition consisting essentially of a polyvinyl butyral resin, a p-toluene-sulfonamide-formaldehyde resin, and a solvent consisting of a combination of ethyl acetate and n-butyl acetate; said solvent being the major constituent of the composition and said p-toluene-sulfonamide-formaldehyde resin being present in an amount no greater than about one part by weight for each part by weight of said polyvinyl butyral resin.

5. The composition of claim 4 wherein said polyvinyl butyral resin is present in an amount of from about 5 to 20% by weight for each 100% by weight of the total composition.

* * * * *